United States Patent [19]

Klaubert et al.

[11] Patent Number: 4,526,978

[45] Date of Patent: Jul. 2, 1985

[54] PROCESS FOR PREPARING 1-H-TETRAZOLE-5-THIOLS AND INTERMEDIATE COMPOUNDS

[75] Inventors: Dieter H. Klaubert, Perkiomenville; John H. Sellstedt, Pottstown, both of Pa.

[73] Assignee: American Home Products Corporation, New York, N.Y.

[21] Appl. No.: 182,728

[22] Filed: Aug. 29, 1980

Related U.S. Application Data

[63] Continuation of Ser. No. 939,517, Sep. 5, 1978, abandoned.

[51] Int. Cl.³ .......................................... C07D 257/04
[52] U.S. Cl. .................................................. 548/251
[58] Field of Search ..................... 548/251; 568/38, 44

[56] References Cited

U.S. PATENT DOCUMENTS 3,962,272  6/1976  Katner ................................ 548/253
4,110,338  8/1978  Kamiya et al.

OTHER PUBLICATIONS

Rappoport, (Ed.), The Chemistry of the Cyano Group, pp. 349-351, Interscience, (1970).
Van Leusen et al., "Tetrahedron Letters", No. 12, pp. 971-973, (1970).
Elderfield, Ed., "Heterocyclic Compounds", vol. 8, pp. 12 & 13, Wiley, N.Y., (1967).
Nirenburg et al., Chem. Abs., 63, Abst. No. 11544a, (1965).
Carpenter, J. Org. Chem., 27, 2085-88, (1965).

Primary Examiner—Glennon H. Hollrah
Assistant Examiner—D. B. Springer
Attorney, Agent, or Firm—Arthur G. Seifert

[57] ABSTRACT

A novel process for producing a 1-H-tetrazole-5-thiol of the formula $$\text{HS}-\underset{\underset{R^1}{|}}{\overset{N=N}{\underset{N}{\overset{||}{C}}}}\overset{N}{\underset{}{}}$$

in which
$R^1$ is hydrogen; lower alkyl; lower alkyl substituted with a carboxylic acid, a carboxylic acid lower alkyl ester, or an hydroxy group; phenyl or phenyl substituted with a halogen, a lower alkyl group, or a lower alkoxy group; benzyl or benzyl substituted with a halogen, a lower alkyl group, or 1-3 alkoxy groups of 1-3 carbon atoms; or trichloroethyl, which process comprises:
(a) reacting a sulfinyl or sulfonyl cyanide of the formula:

$$RS(O)_nCN$$

in which
n is 1 or 2 and
R is alkyl; phenyl or phenyl substituted with a halogen, a lower alkyl group, or a lower alkoxy group; benzyl or benzyl substituted on the phenyl ring with a halogen, a lower alkyl group, or a lower alkoxy group; or an alicyclic group, with an azide of the formula $R^1N_3$, in which $R^1$ is as defined above, to form a 5-sulfinyl or sulfonyl-1-H-tetrazole of the formula:

$$\text{RS(O)}_n-\underset{\underset{R^1}{|}}{\overset{N=N}{\underset{N}{\overset{||}{C}}}}\overset{N}{\underset{}{}}$$

in which
n is 1 or 2, and
R and $R^1$ are as defined above, and
(b) reacting said 5-sulfinyl or sulfonyl-1-H-tetrazole with an alkali metal sulfide or ammonium sulfide.

3 Claims, No Drawings

PROCESS FOR PREPARING 1-H-TETRAZOLE-5-THIOLS AND INTERMEDIATE COMPOUNDS

CROSS-REFERENCE TO COPENDING APPLICATION

This application is a continuation of copending application Ser. No. 939,517, filed Sept. 5, 1978, abandoned.

SUMMARY OF THE INVENTION

Applicants have discovered a novel process for the production of 1-H-tetrazole-5-thiols which have the following structural formula:

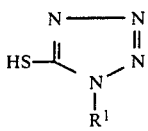

wherein:

$R^1$ is hydrogen; lower alkyl; lower alkyl substituted with a carboxylic acid, a carboxylic acid lower alkyl ester, or a hydroxy group; phenyl or phenyl substituted with a a halogen, a lower alkyl group, or a lower alkoxy group; benzyl or benzyl substituted with a halogen, a lower alkyl group, or 1–3 alkoxy groups of 1–3 carbon atoms; or trichloroethyl.

Applicants' novel process involves two steps: viz.

(a) reacting a sulfinyl or sulfonyl cyanide of the formula $RS(O)_nCN$ with an azide of the formula $R^1N_3$ to form an intermediate 5-sulfinyl or sulfonyl-1-H-tetrazole of the formula:

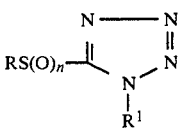

wherein
n is 1 or 2,
$R^1$ is as defined above, and
R is alkyl; phenyl or phenyl substituted with a halogen, a lower alkyl group, or a lower alkoxy group; benzyl or benzyl substituted on the phenyl ring with a halogen, a lower alkyl group, or a lower alkoxy group; or an alicyclic group, and (b) reacting said 5-sulfinyl or sulfonyl-1-H-tetrazole with an alkali metal sulfide or ammonium sulfide thereby causing the displacement of the sulfinyl or sulfonyl group with the sulfide and thereby forming the desired 1-H-tetrazole-5-thiol.

A second process aspect of Applicants' invention is the reaction of a sulfinyl or sulfonyl cyanide of the formula $RS(O)_nCN$ with an azide of the formula $R^1N_3$ to yield a 5-sulfinyl or sulfonyl-1-H-tetrazole (n, R and $R^1$ being as defined above).

A third process aspect of Applicants' invention is the reaction of a 5-sulfinyl or sulfonyl-1-H-tetrazole with an alkali metal sulfide or ammonium sulfide to form a 1-H-tetrazole-5-thiol.

A fourth aspect of Applicants' invention comprises the intermediate 5-sulfinyl or sulfonyl-1-H-tetrazole compounds of the formula:

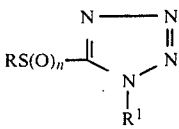

in which n=1 or 2, and R and $R^1$ are as defined earlier.

The 1-H-tetrazole-5-thiols formed by the processes of the invention are useful as intermediates in the preparation of various cephalosporins and penicillins.

SPECIFICATION

Numerous cephalosporins are reported which contain a (1-H-tetrazole-5-thio)methyl group at the 3-position of the 7-aminocephalosporanic acid ring. Two well known examples, cefamandole and cefazaflur, both contain a (1-methyl-tetrazole-5-thio)methyl group at the 3-position. Other examples of cephalosporins utilizing such tetrazole-5-thiol "tails" may be found in U.S. Pat. Nos. 3,516,997 and 3,530,123 and in Belgian Brevet D' Invention Nos., 856636 and 856637. Such cephalosporins (and penicillins which also utilize the tetrazole-5-thiol tails) exhibit a broad spectrum of antibiotic activity.

Finnegan et al., J. Am. Chem. Soc., 80, 3908 (1958) describe the reaction of certain alkyl and aryl nitriles with certain azide salts such as ammonium, substituted ammonium, sodium and lithium azides to form 5-substituted tetrazoles. Carpenter, J. Org. Chem., 27, 2085 (1962) describes the reaction of perhaloalkylnitriles with aliphatic and phenyl azides to form 1,3-disubstituted tetrazoles. The perhaloalkyl groups were chosen for this reaction study by Carpenter because of their characteristic as electron withdrawing groups. Additionally, in U.S. Pat. No. 3,962,272 (1976) Katner described the production of 5-acyl-tetrazole-1-acetate esters by the reaction of an acyl cyanide with an azidoacetic acid or ester at elevated temperatures.

The synthesis of sulfonyl cyanides was first reported by Cox and Ghosh in Tetrahedron Letters, 39, 3351 (1969). A. M. van Leusen and J. C. Jagt thereafter described various reactions of the sulfonyl cyanides in a series of papers. See for example, "Nucleophilic Displacements On Sulfonyl Cyanides", Tetrahedron Letters, 12, 967 (1970); "Diels-Alder Cycloadditions Of Sulfonyl Cyanides With Dienes", Recueil, 92, 1343 (1973); "Formation of C-(arylsulfonyl)- and C-(alkylsulfonyl)formamidrazones and their Conversion to 1,2,4-Triazoles", Recl. Trav. Chim. Pays-Bas, 92, 12 (Eng., 1975); and "Diels-Alder Cyclo additions of Sulfonyl cyanides with Cyclopentadiene. Synthesis of 2-Azabicyclo[2.2.1]hepta-2,5-dienes", J. Org. Chem., 39, 564 (1974). The synthesis of sulfinyl cyanides was first reported by Boerma-Markerink et al. in Synthetic Communications, 5, 147 (1975).

Applicants' process for the formation of 1-H-tetrazole-5-thiols is shown in the two-step reaction diagram below:

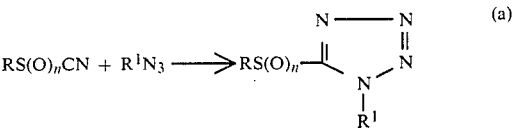

(a)

-continued

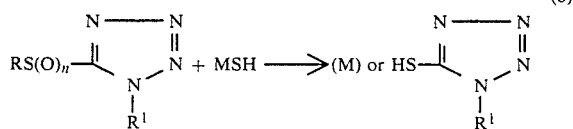
(b)

in which n is 1 or 2; R and $R^1$ are as defined above; and M is an alkali metal ion or ammonium ion.

The particular reaction conditions for reaction (a) are not critical. For example, reaction (a) may be run in a sealed bomb or in an open vessel, depending upon the temperatures required and the boiling points of the reactants and of the solvent. The reaction may be carried out at elevated temperatures or at room temperatures, and the time of the reaction will usually vary with the temperatures utilized. An inert organic solvent such as benzene, n-hexane or a halocarbon is used.

Nor, are the reaction conditions for reaction (b) critical. Reaction (b) may be carried out at room temperatures or at slightly elevated temperatures, and the reaction time will usually be dependent upon the temperature conditions. The reaction is conveniently run using an aprotic solvent such as acetone or acetonitrile.

Where $R^1$=hydrogen is desired in the 1-H-tetrazole-5-thiol final product, two reaction routes are possible. First, in reaction (a) a compound wherein $R^1$=benzyl, 4-methoxybenzyl, 2,4-dimethoxybenzyl, or 2,4,6-trimethoxybenzyl may be used yielding the intermediate 5-sulfinyl or sulfonyl-1-H-tetrazole and the 1-H-tetrazole-5-thiol with such $R^1$ group at the 1-position. The resultant 1-H-tetrazole-5-thiol product subsequently formed in reaction (b) may then be treated with a strong acid or under hydrogenation conditions to deprotect the 1-position by removal of the benzyl, 4-methoxybenzyl, 2,4-dimethoxybenzyl or 2,4,6-trimethoxybenzyl group. Thus said benzyl and methoxybenzyl groups may serve as the desired final substituents at the 1-position of the 1-H-tetrazole-5-thiol or they may serve as protecting groups to be removed at the end of the reaction sequence to yield tetrazole-5-thiol.

Alternatively, the 1-H-tetrazole-5-thiol in which $R^1$=hydrogen, namely tetrazole-5-thiol, may be obtained by choosing $R^1$=hydrogen in reaction (a)—i.e. using hydrozoic acid as the azide reactant—thus forming the intermediate 5-sulfinyl or sulfonyl-1-H-tetrazole with a hydrogen atom at the 1-position. Before reacting this product with the alkali metal sulfide or ammonium sulfide of reaction step (b), the 1-position would have to be protected against reaction with the sulfide. The protecting group used must be inert to reaction with the sulfide and, after reaction (b) has been completed, must be readily removable under conditions which will not disturb the remainder of the molecule. Such protection and deprotection of the 1-position is well within the skill of the art. The benzyl, 4-methoxybenzyl, 2,4-dimethoxybenzyl, and 2,4,6-trimethoxybenzyl groups described above are also convenient proprotecting groups in this alternative protection sequence. The benzyl or methoxybenzyl group may be added to 5-sulfinyl or sulfonyl-1-H-tetrazole by reacting the tetrazole with a benzylhalide or a methoxybenzyl halide, respectively, in the presence of an acid scavenger, such as potassium carbonate, triethylamine, or sodium hydroxide. The benzyl or methoxybenzyl groups are readily removable using a strong acid or under hydrogenation conditions. Another example of a protecting group useful in this alternative protection reaction sequence is the trichloroethyl group, which is formed by the reaction of trichloroethyl bromide with 5-sulfinyl or sulfonyl-1-H-tetrazole. Removal of the trichloroethyl group is accomplished by reacting the protected tetrazole-5-thiol with zinc in acetic acid, tetrahydrofuran, methanol, or water.

Since the hydrogen on a 5-substituted tetrazole may reside at either the 1- or 2-position of the tetrazole ring, the protecting group in these latter reactions may attach to the tetrazole ring at either the 1- or 2-position. However, the net affect is the same: viz., the sulfide in reaction (b) reacts only at the 5-position, displacing the sulfinyl or sulfonyl group, and the subsequent deprotection with a strong acid or hydrogen yields tetrazole-5-thiol. On the other hand, in the first-mentioned protecting process which utilizes the benzyl or methoxybenzyl groups as the initial azide reactant, the placement of the protecting group ($R^1$=benzyl or methoxybenzyl) is specific for the 1-position and no such ambiguity exists as to which position is being protected.

The first-mentioned process using the benzyl or methoxybenzyl groups as the initial azide reactant is the preferred reaction sequence to form tetrazole-5-thiol.

With respect to removal of the benzyl or methoxybenzyl protecting groups, liquid hydrogen fluoride or trifluoroacetic acid, in anisole or other carbonium ion scavenger, are examples of strong acids used to effect such removal. Hydrogenation conditions normally used to effect removal are the bubbling of hydrogen gas through a palladium on charcoal catalyst in ethanol, ethylacetate, or acetic acid.

The 1-H-tetrazole-5-thiol compounds produced by the processes of the invention are commonly employed in the production of cephalosporins by reaction with 7-aminocephalosporanic acid resulting in the displacement of the acetoxyl group at the 3-position by the thiol. Thus, a (1-H-tetrazole-5-thio)methyl tail is formed at the 3-position of the 7-aminocephalosporanic acid (or derivative). The novel 5-sulfinyl or sulfinyl-1-H-tetrazoles disclosed herein are, of course, useful as intermediates in the production of said 1-H-tetrazole-5-thiols.

As used herein, the term "alkyl" refers to aliphatic hydrocarbon groups containing from 1 to 10 carbon atoms. The term "lower alkyl" refers to aliphatic hydrocarbon groups containing from 1 to 6 carbon atoms. The term "lower alkoxy" refers to alkoxy groups containing from 1 to 6 carbon atoms. An "alkoxy group of 1–3 carbon atoms" refers to methoxy, ethoxy, n-propoxy, or isopropoxy; methoxy and ethoxy being preferred. "Halogen" refers to fluorine, chlorine, bromine or iodine; and chlorine and bromine are preferred halogens.

An "alicyclic group" means a saturated cyclic hydrocarbon group having 5–10 carbon atoms, including monocyclic, bicyclic and tricyclic groups. Examples of such alicyclic groups include cyclopentyl, cyclohexyl, cycloheptyl, cyclooctyl, decalinyl, bicycloheptyl, bicyclooctyl, and adamantyl.

Preferred R groups are the p-tolyl, benzyl, hexyl, and 1-adamantyl groups. Preferred $R^1$ groups are the methyl, ethoxycarbonylmethyl, benzyl, and 4-methoxybenzyl groups. 2,4-dimethoxybenzyl and 2,4,6-trimethoxybenzyl are further preferred $R^1$ groups.

The following examples further illustrate the best mode contemplated by the inventors for the practice of the invention.

EXAMPLE 1

1-Methyl-5-p-Toluenesulfonyltetrazole

A mixture of 36.2 g. (0.2 mol.) of p-toluenesulfonyl cyanide [M. J. Cox and R. Ghosh, Tet. Letters, 3351 (1969)] and 50 g. (0.9 mol.) of methyl azide [O. Dimroth, Ber., 38, 1572 (1905)] in 100 ml. of benzene is heated in a sealed bomb at 80° for 4 hours. The reaction mixture is filtered and allowed to cool to give 42 g. of crystallize product, m.p. 110°–111° C.

Analysis for: $C_9H_{10}N_4O_2S$: Calculated: C, 45.36; H, 4.23; N, 23.52. Found: C, 45.58; H, 4.15; N, 23.89.

EXAMPLE 2

1-Ethoxycarbonylmethyl-5-p-Toluenesulfonyltetrazole

A mixture of 7.24 g. of p-toluenesulfonyl cyanide and 5.16 g. of ethyl azidoacetate (Dictionary of Organic Compounds, Vol. 1, p. 307) in 150 ml. of benzene is heated at reflux for 12 hours. The residue after evaporation is recrystallized from benzene-hexane, m.p. 98°–100° C.

Analysis for: $C_{12}H_{14}N_4O_4S$: Calculated: C, 46.44; H, 4.55; N, 18.05. Found: C, 46.38; H, 4.24; N, 17.99.

EXAMPLE 3

5-p-Toluenesulfonyltetrazole

A mixture of p-toluenesulfonyl cyanide (0.0 g.) and excess hydrazoic acid in 50 ml. of benzene is stirred at room temperature for 20 hours. The product is filtered off, dissolved in ether, filtered through celite and evaporated to a solid which on trituration with benzene has a melting point, 133°–135° C.

Analysis for: $C_8H_8N_4SO_2$: Calculated: C, 42.85; H, 3.59; N, 24.99. Found: C, 42.43; H, 3.51; N, 25.07.

EXAMPLE 4

1-p-Methoxybenzyl-5-p-Toluenesulfonyltetrazole

The title compound is prepared as in Example 2 using p-methoxybenzyl azide [Fr. Moulin, Helv. Chim. Acta, 35, 167 (1952)], m.p. 125°–126° C.

Analysis for: $C_{16}H_{16}N_4O_3S$: Calculated: C, 55.80; H, 4.68; N, 16.27. Found: C, 55.95; H, 4.69; N, 16.16.

EXAMPLE 5

1-Methyl-5-Phenylmethanesulfonyltetrazole

This material is prepared as in Example 1 using benzylsulfonyl cyanide (Cox and Ghosh, loc. cit.) instead of p-toluenesulfonyl cyanide, m.p. 122°–125° C., from benzene-hexane.

Analysis for: $C_9H_{10}N_4O_2S$: Calculated: C, 45.36; H, 4.23; N, 23.52. Found: C, 45.54; H, 4.17; N, 23.41.

EXAMPLE 6

1-Ethoxycarbonylmethyl-5-Phenylmethanesulfonyltetrazole

The title compound is prepared as in Example 2 using benzylsulfonyl cyanide, m.p. 105°–107° C.

Analysis for: $C_{12}H_{14}N_4O_4S$: Calculated: C, 46.44; H, 4.55; N, 18.05. Found: C, 46.65; H, 4.46; N, 18.12.

EXAMPLE 7

5-Phenylmethanesulfonyltetrazole

The use of benzylsulfonyl cyanide as in Example 3 gives the title compound which is recrystallized from ethyl acetatehexane, m.p. 135°–137° C.

Analysis for: $C_8H_8N_4O_2S$: Calculated: C, 42.85; H, 3.59; N, 24.99. Found: C, 42.97; H, 3.59; N, 25.05.

EXAMPLE 8

1-Benzyl-5-Phenylmethanesulfonyltetrazole

Heating a mixture of benzyl azide (Fr. Moulin, loc. cit.) and benzylsulfonyl cyanide as in Example 2 gives the title compound, m.p. 94°–96° C.

Analysis for: $C_{15}H_{14}N_4O_2S$: Calculated: C, 57.31; H, 4.40; N, 17.82. Found: C, 57.29; H, 4.35; N, 17.68.

EXAMPLE 9

1-Ethoxycarbonylmethyl-5-Hexylsulfonyltetrazole

Substituting hexanesulfonyl cyanide (Cox and Ghosh, loc. cit.) in Example 2 results in the formation of the title compound which is recrystallized from hexane, m.p. 40°–42° C.

Analysis for: $C_{11}H_{20}N_4O_4S$: Calculated: C, 43.40; H, 6.62; N, 18.41. Found: C, 43.40; H, 6.68; N, 18.41.

EXAMPLE 10

1-Ethoxycarbonylmethyl-5-(1-Adamantane)Sulfinyltetrazole

Replacement of p-toluenesulfonyl cyanide with 1-adamantanesulfinyl cyanide [A. M. van Leusen et al., Synth. Commun., 5, 147 (1975)] in Example 2 results in the formation of the desired product, from hexane, m.p. 60°–62° C.

Analysis for: $C_{15}H_{22}N_4O_3S$: Calculated: C, 53.23; H, 6.55; N, 16.56. Found: C, 53.25; H, 6.67; N, 16.40.

EXAMPLE 11

1-Ethoxycarbonylmethyl-5-Tetrazolethiol

A mixture of the product in Example 2 and an equal weight of sodium sulfhydrate in acetone is stirred for 4 hours. The insolubles are filtered off and the filtrate is evaporated to dryness. The residue is suspended in methylene chloride, washed with dil. HCl, dried and evaporated. The residue is recrystallized from benzene-hexane, m.p. 93°–95° C.

Analysis for: $C_5H_8N_6O_2S$: Calculated: C, 31.91; H, 4.28; N, 29.77. Found: C, 32.09; H, 4.40; N, 29.48.

EXAMPLE 12

1-Methyl-5-Tetrazolethiol

A mixture of the product of Example 1 and sodium sulfhydrate as in Example 11 is stirred for 4 hours. The insolubles are removed by filtration and the filtrate is taken to dryness. The residue is recrystallized from acetonitrile to give the title compound as a sodium salt, m.p. 250°–255° C. (decomp).

Analysis for: $C_2H_3N_4SNa.\frac{1}{3}H_2O$: Calculated: C, 16.66; H, 2.57; N, 38.87. Found: C, 17.32; H, 2.42; N, 38.24.

EXAMPLE 13

1-p-Methoxybenzyl-5-Tetrazolethiol

Treatment of the product of Example 4 as in the previous example gives the sodium salt of the title compound. This is recrystallized from ethyl acetate-hexane, m.p. 246°–250° C. (decomp).

Analysis for: $C_9H_9N_4SONA.1/5H_2O$: Calculated: C, 43.61; H, 3.82; N, 22.61. Found: C, 43.90; H, 3.63; N, 22.54.

What is claimed is:

1. A 5-sulfinyl or sulfonyl-1-H-tetrazole compound of the formula:

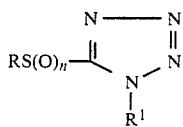

in which
n is 1 or 2;
R is phenyl or phenyl substituted with a halogen, a lower alkyl group, or a lower alkoxy group; or a saturated alicyclic hydrocarbon group having 5–10 carbon atoms, and
$R^1$ is hydrogen; lower alkyl; lower alkyl substituted with a carboxylic acid group, a carboxylic acid lower alkyl ester group, or an hydroxy group; phenyl or phenyl substituted with a halogen, a lower alkyl group, or a lower alkoxyl group; benzyl or benzyl substituted with a halogen, a lower alkyl group, or 1–3 alkoxy groups of 1–3 carbon atoms; or trichloroethyl,
wherein lower alkyl and lower alkoxy refers to such groups having 1–6 carbon atoms.

2. A compound according to claim 1 wherein R is selected from a group consisting of p-tolyl, n-hexyl, and 1-adamantyl.

3. A compound according to claim 1 wherein $R^1$ is selected from a group consisting of hydrogen, methyl, ethoxycarbonyl, benzyl, 4-methoxybenzyl, 2,4-dimethoxybenzyl, and 2,4,6-trimethoxybenzyl.

* * * * *